United States Patent
Schuster

[11] 4,025,587
[45] May 24, 1977

[54] AIR HUMIDIFIER

[75] Inventor: Donald R. Schuster, Columbus, Ohio

[73] Assignee: White-Westinghouse Corporation, Cleveland, Ohio

[22] Filed: Feb. 3, 1976

[21] Appl. No.: 654,951

Related U.S. Application Data

[63] Continuation of Ser. No. 459,738, April 10, 1974, abandoned.

[52] U.S. Cl. .................................. 261/30; 55/259; 261/90; 261/92; 261/105
[51] Int. Cl.² .......................................... B01F 3/04
[58] Field of Search ................. 261/28, 30, 35, 90, 261/92, 29, 34 R, DIG. 15, 89; 126/113; 55/225, 230, 259, 246–249; 62/279, 280

[56] References Cited

UNITED STATES PATENTS

| | | | |
|---|---|---|---|
| 2,710,510 | 6/1955 | Roseman | 261/35 X |
| 2,793,510 | 5/1957 | Komroff et al. | 62/280 |
| 3,045,449 | 7/1962 | Durdle | 62/279 |
| 3,079,766 | 3/1963 | Abbott et al. | 55/225 X |
| 3,159,984 | 12/1964 | Eberhart et al. | 62/279 |
| 3,304,066 | 2/1967 | Vieceli et al. | 261/29 |
| 3,348,822 | 10/1967 | Vieceli et al. | 261/34 R |
| 3,359,967 | 12/1967 | Homkes | 126/113 |
| 3,637,194 | 1/1972 | Swimmer et al. | 261/92 X |
| 3,724,233 | 4/1973 | Pugh et al. | 62/280 X |
| 3,730,497 | 5/1973 | Schmitt et al. | 261/92 |
| 3,766,751 | 10/1973 | Ball | 62/279 X |
| 3,770,254 | 11/1973 | Morrow | 261/DIG. 15 |

*Primary Examiner*—Tim R. Miles
*Assistant Examiner*—Richard L. Chiesa
*Attorney, Agent, or Firm*—Strauch, Nolan, Neale, Nies & Kurz

[57] ABSTRACT

An air humidifier for adding moisture to air by aspiration. The humidifier contains a fan surrounded by a shroud having an aspirator duct near its bottom on its low pressure side. The fan draws small droplets of water from a water reservoir disposed beneath the aspirator duct into the flow of air created by the fan. The air flow then passes through an evaporative filter wherein the water is dispersed and evaporated into the air flow and mineral content of the water is substantially filtered from the air flow.

4 Claims, 5 Drawing Figures

AIR HUMIDIFIER

CROSS-REFERENCE TO RELATED APPLICATION

This application is a continuation of application Serial No. 459,738, filed April 10, 1974 and now abandoned.

BACKGROUND OF THE INVENTION

1. FIELD OF THE INVENTION

This invention pertains to the art of humidifiers, and more particularly to humidifiers of the type used to humidify the air in a particular room.

2. DESCRIPTION OF THE PRIOR ART

None of the prior art of which the applicant is aware uses a fan induced aspiration process to deposit water on a stationary evaporative media. However, patents such as U.S. Pat. Nos. 3,348,822; 3,304,066 teach the use of other means to transfer water from a reservior to an evaporative medium. In addition U.S. Pat. No. 3,359,967 utilizes a fan system to move water from a sump into the air flow created by the fan. However, this system does not include a downstream pad and the water is introduced into the air flow from a position which causes the water to be moving in the same direction as the air from its introduction. The water is dispersed by a rotating disc on the fan shaft upstream from the fan.

Some of the structure of the present invention is somewhat similar to that found in U.S. Pat. No. 3,159,984, covering a condensate disposal system in a room air conditioner.

SUMMARY OF THE INVENTION

The air humidifier provided by this invention comprises a shroud surrounding a fan, a sump for water located below the bottom of the shroud, means to control the water level in the sump, an aspirator duct located adjacent to the bottom of said shroud on the low pressure side of the shroud and providing a water passage from the sump to the suction side of the fan. Water is drawn through the duct when the fan rotates and this water is dispersed in the air flow created by the fan. An evaporative filter is positioned to intersect the flow of air created by the fan. The air flow passes through the evaporative filter resulting in further dispersement, and evaporation of the water added to the air flow. The evaporative filter also substantially filters from the air flow minerals and solids introduced by the water.

DESCRIPTION OF THE PREFERRED EMBODIMENTS

Figure 1:
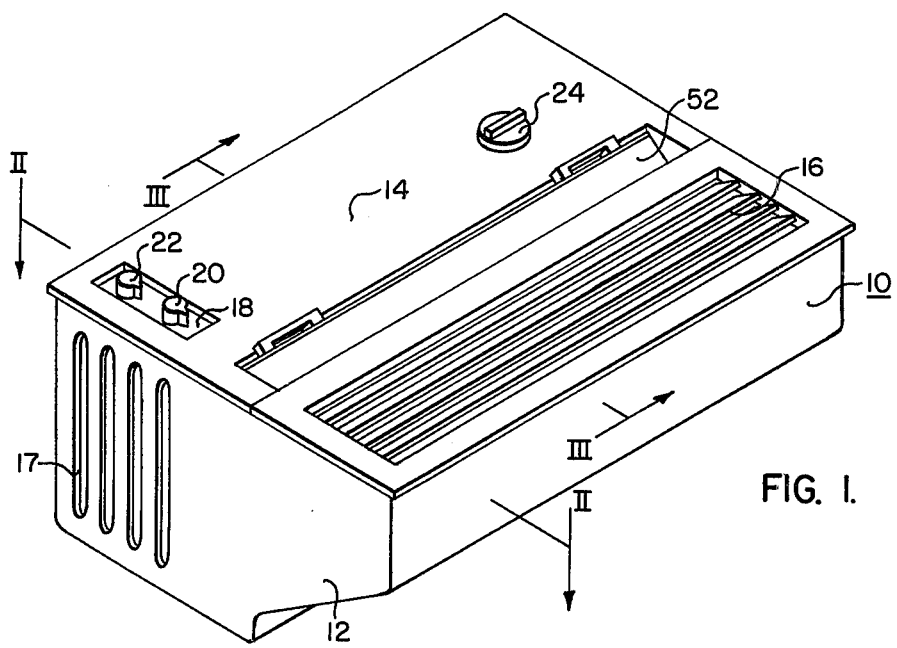
FIG. 1 is an isometric view of a table model humidifier embodying the invention.

Referring to FIG. 1, a portable humidifier 10 of the type suitable for table or desk top as well as floor use is shown. The humidifier 10 includes a cabinet 12 and a top 14. An air flow exhaust grille 16 entends over a considerable portion of the top 14 providing an ample portal from which the humidified air can be exhausted. An air intake grille 17 is located in the side of the cabinet 12. A control panel 18 is also included as part of the top having a humidistat control 20, a fan control 22, and a water level indicator and water fill opening 24.

Figure 2:
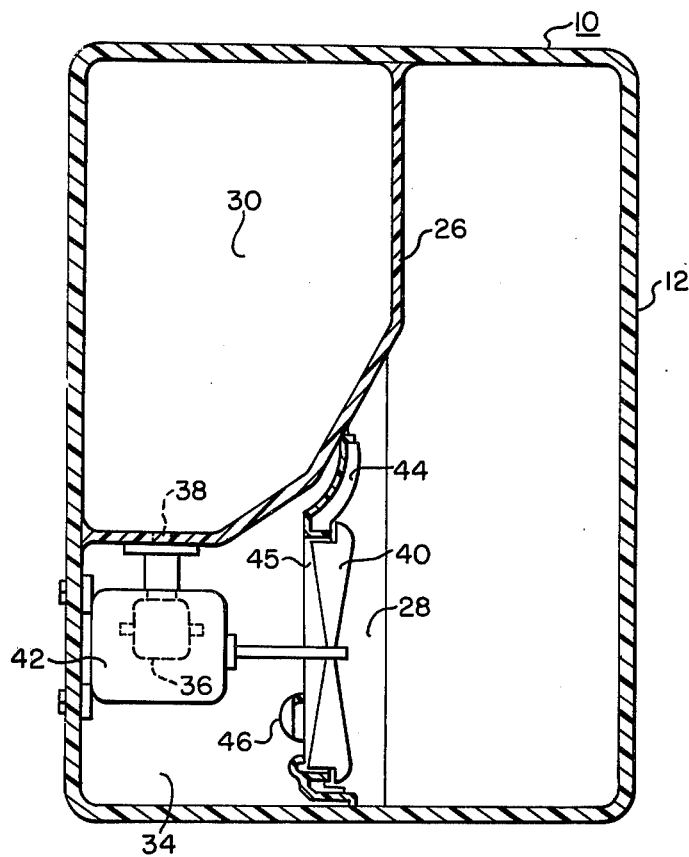
FIG. 2 is a sectional view taken along line II—II of FIG. 1.
Figure 3:
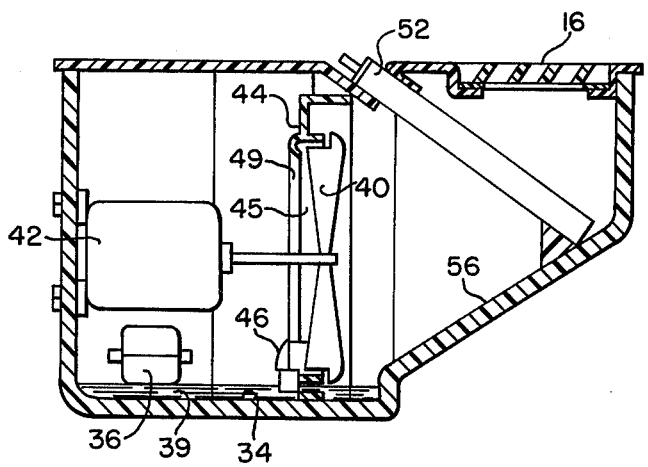
FIG. 3 is a sectional view taken along line III—III of FIG. 1.

The details of the humidifier 10 are better shown in FIGS. 2 and 3. In the preferred embodiment, the cabinet 12 is a unitary construction made from molded plastic. The cabinet 12 is divided by a partition 26. The partition is attached to the walls of the cabinet 12. The partition 26 and the cabinet 12 together define a first compartment 28 and a second compartment 30 which functions as a water reservoir. The water reservoir 30 supplies a sump 34 located on the bottom of the cabinet 12 in the first compartment 28. The level of water in the sump 34 supplied from the reservoir 30 is controlled by the float valve 36. The float valve 36 is mounted on the partition 26 sufficiently above the bottom of the cabinet 12 to maintain the desired level of water in the sump 34 by opening and closing a port 38 in the partition 26 in response to the water level 39 in the sump 34. The fan 40, driven by an electric motor 42, is positioned within the first compartment 28. The fan 40 is partly surrounded by a shroud 44 which is attached to the cabinet 12 and the partition 26. The circular opening 45 in the shroud has a diameter sufficient to provide a slight clearance for the outside diameter of the fan 40. An aspirator duct 46 is made a part of the shroud 44 and is positioned on the low pressure or motor side thereof. The aspirator duct 46 might also be a separate part from the shroud and attached thereto.

Figure 4:
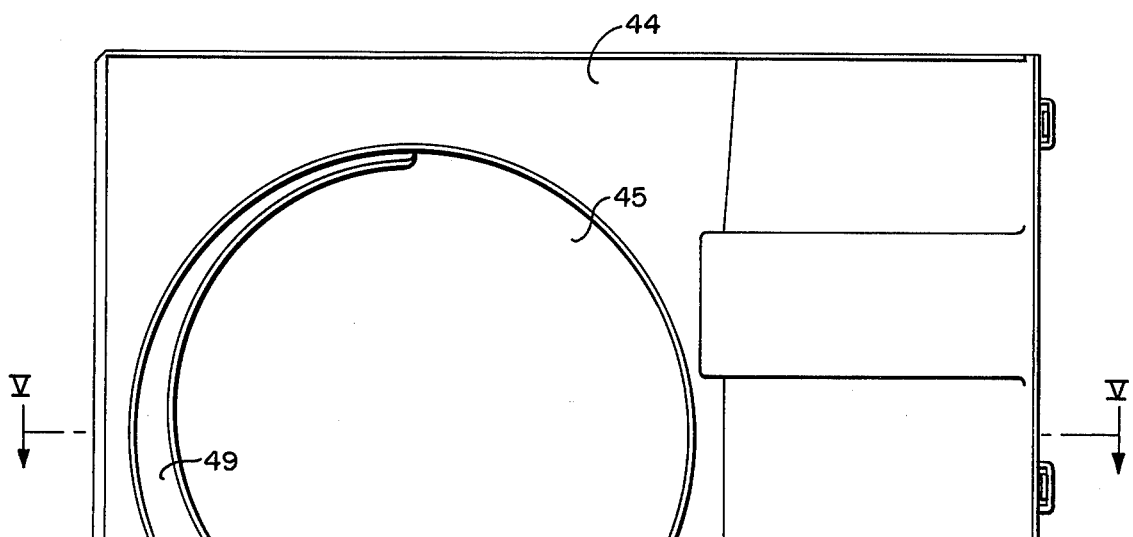
FIG. 4 is an enlarged elevational view of the shroud as viewed from the downstream side of the fan; and, FIG. 5 is a sectional view taken along line V—V of FIG. 4.
Figure 5:
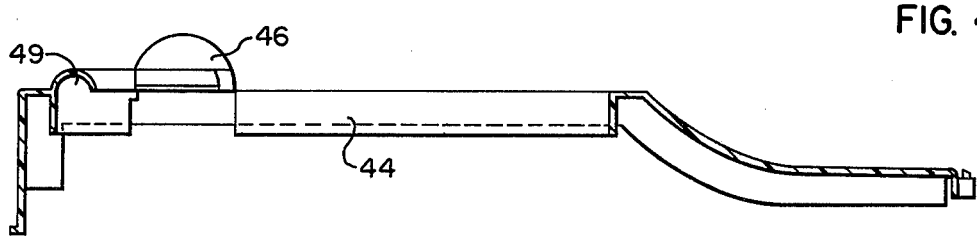

The aspirator duct 46 and shroud 44 are best shown in FIGS. 4 and 5. In the preferred embodiment the aspirator duct 46 is an open spaced channel comprised of a downwardly opened bowl portion 48 which at its top opens onto a scroll portion 49 which scroll portion 49 extends a part of the way around the circumference of the shroud opening 45 and terminates near the top of the shroud opening 45. The scroll portion 49 has a generally semicircular cross sectional shape with the concavity facing the fan. The cross section gradually diminishes with the circumferential distance removed from the bowl portion 48. During normal operations, the top surface of the water 39 in FIG. 3, contained in the sump 34, is maintained by the float value 36 to be at or near the bottom edge 47 of the opening of the bowl portion 48.

When the motor 42 rotates the fan 40 an air flow is created through the opening 45 in the shroud 44 from the motor side of the shroud into the first compartment 28 on the fan side of the shroud. The way in which water is lifted from the sump is believed to be generally as follows. The air flow creates a pressure differential in the bowl portion 48 of the aspirator 46. A relatively lower pressure exists in the upper part of the bowl 48 than exists at the bottom opening 48 at the surface of the water 39. This results in a suction effect on the water. The suction effect along with the air flow created by the fan cause minute droplets of water to be forced from the surface of the water through the bowl portion 48 and scroll portion 49 into the air flow created by the fan 40. These droplets are dispersed into the air flow and thrown by the fan 40 to be deposited on a porous evaporative filter pad 52. The evaporative filter pad 52 covers substantially the entire area of the air flow path. The scroll portion 49 also serves as a baffle to deflect water thrown radially by the fan back into the air flow. When the water is deposited on the porous evaporative filter pad 52 further dispersement, and evaporation of the droplets into the air flow occurs.

A significant advantage is obtained by routing the humidified air flow through the evaporative filter pad 52 in that any minerals and foreign materials carried by the water are filtered from the water by the filter pad 52. The humidified air which passes from the filter through the air grille 16 exiting into the room to be humidified, is substantially free from dissolved foreign matter.

The filter pad 52 can be slidably removed through the top 14 for cleaning or replacement. With the filter 52 positioned in the cabinet 12 as shown any excess water deposited thereon will drip back onto the inclined drip surface 56 and then onto the bottom of compartment 28 which serves as the sump 34.

Alternate constructions of the humidifier could utilize an inverted bottle, barometric pressure controlled, water source in place of the reservoir and float valve. A drain valve would then be included in the cabinet near the sump for draining when overfilled.

From the foregoing description taken with the drawings, it is seen that this invention has provided a new and improved apparatus for humidifying an air flow.

I claim:

1. An apparatus for adding humidity to an air flow comprising; an axial flow fan; motor means for rotating said fan; a shroud substantially surrounding said fan for assuring that a relatively lower pressure exists on the upstream side of said fan when said fan operates by impeding air flow from the downstream to the upstream side of said fan; a sump adapted to be supplied with water, said sump disposed below said shroud; a continuous channel shaped duct means comprising a concave bowl portion adjacent said sump and a concave scroll portion extending partly around the fan opening within the periphery of said shroud and extending upwardly from in fluid flow communication with said bowl portion, said duct means connected with the shroud and located within the periphery of the shroud with its open side of the channel shape facing the upstream or low pressure side of said fan and with a part of the bowl portion opening at or near the water surface level of said sump, so that said channel shaped concave duct communicates said lower pressure with said sump when said fan rotates causing water to be aspirated through said bowl portion and along said scroll portion from said sump and dispersed by said fan into the exhaust of said fan; said scroll portion gradually decreasing in cross-sectional area from the sump up to a location adjacent the top of the shroud where it merges with said shroud so that the water dispersed radially by said fan is redirected into said air flow by said scroll portion; and a porous pad positioned downstream from said fan to intersect said exhaust causing additional dispersement of said water and substantially filtering from said water matter and foreign particles carried therein.

2. The apparatus of claim 1, wherein: said shroud, said bowl and said scroll portion are one piece.

3. The apparatus of claim 1, wherein means located between said porous pad and said sump provide a path for excess water to flow from said pad to said sump.

4. The apparatus of claim 3, wherein said means providing a path for flow of excess water from said pad is an inclined wall connected to said sump and located adjacent said pad in a position whereby water dripping from said pad falls on the inclined wall and flows into the sump.

* * * * *